United States Patent [19]

Diehr

[11] 4,334,073
[45] Jun. 8, 1982

[54] PROCESS FOR THE PREPARATION OF ALPHA-HYDROXYCARBOXYLIC ACID AMIDE COMPOUNDS

[75] Inventor: Hans-Joachim Diehr, Wuppertal, Fed. Rep. of Germany

[73] Assignee: Bayer Aktiengesellschaft, Leverkusen, Fed. Rep. of Germany

[21] Appl. No.: 211,989

[22] Filed: Dec. 1, 1980

Related U.S. Application Data

[63] Continuation-in-part of Ser. No. 114,469, Jan. 23, 1980, abandoned.

[30] Foreign Application Priority Data

Feb. 7, 1979 [DE] Fed. Rep. of Germany ....... 2904490

[51] Int. Cl.³ .................... C07D 211/16; C07D 85/24
[52] U.S. Cl. ............................. 546/245; 260/239 B; 544/164; 544/176; 546/19; 546/146; 546/156; 548/200; 548/214; 564/201; 564/202; 564/203; 548/452; 548/491; 548/540; 549/472; 549/493
[58] Field of Search ................. 544/164, 176; 546/19, 546/146, 156, 245; 548/200, 214; 564/201, 202, 203; 260/347.3, 326.5 E, 239 B, 326.16, 326.5 B

[56] References Cited

U.S. PATENT DOCUMENTS 3,898,262 8/1975 Fischer et al. .................... 71/103 X

OTHER PUBLICATIONS

*Chemical Abstracts,* 78:158976t (1973) [German Ols 2,245,457, 3/22/73, Bourgav et al].
March, J., *Advanced Organic Chemistry,* McGraw Hill, New York, 1968, pp. 322–323.

*Primary Examiner*—Richard A. Schwartz
*Attorney, Agent, or Firm*—Sprung, Felfe, Horn, Lynch & Kramer

[57] ABSTRACT

Process for the preparation of an alpha-hydroxycarboxylic acid amide compound of the formula

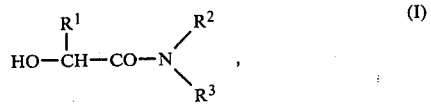
(I)

wherein
$R^1$ is hydrogen or alkyl; and
$R^2$ and $R^3$ are individually selected from hydrogen, alkyl, alkenyl, alkynyl, aralkyl, cycloalkyl or aryl, each of which may be optionally substituted, or a nitrogen-containing heterocyclic radical; or
$R^2$ and $R^3$, together with the nitrogen atom to which they are bonded, represent an optionally benzo-fused monocyclic or bicyclic ring, which ring may be substituted and may be partially unsaturated, which process comprises reacting in a first stage an alpha-halocarboxylic acid amide of the formula

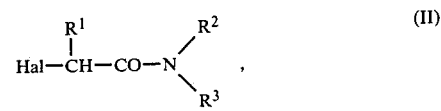
(II)

wherein
$R^1$, $R^2$ and $R^3$ are identified as above; and
Hal is chlorine or bromine, with an alkali metal acetate or alkaline earth metal acetate in the presence of a quaternary ammonium salt at a temperature between 20° and 200° C., and, in a second stage, deacylating the alpha-acetoxycarboxylic acid amide produced, having the general formula

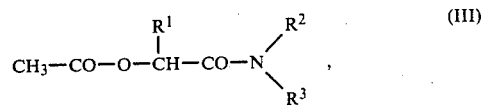
(III)

in which $R^1$, $R^2$ and $R^3$, are identified as above by reacting said amide III with an alcohol of the general formula

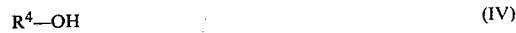

$R^4$—OH (IV)

in which $R^4$ is alkyl in the presence of a catalytic amount of a catalyst selected from alkali metal hydroxides, alkaline earth metal hydroxides, alkali metal carbonates, and alkaline earth metal carbonates, at a temperature between 20° and 150° C., these compounds are useful as intermediates in the preparation of herbicides, e.g., substituted sulfonyl glycol amides and anilides.

16 Claims, No Drawings

PROCESS FOR THE PREPARATION OF ALPHA-HYDROXYCARBOXYLIC ACID AMIDE COMPOUNDS

This is Continuation-in-Part of Ser. No. 114,469 filed Jan. 23, 1980 (now abandoned).

The invention relates to a process for the preparation of certain alpha-hydroxycarboxylic acid amide compounds. Such compounds are useful as intermediates in the preparation of herbicides, e.g., substituted sulfonyl glycol amides and anilides.

It is known that a glycollic acid anilide is obtained when a chloroacetic acid anilide is reacted with an acetate to give an acetoxyacetic acid anilide and the latter is saponified under alkaline conditions (see DE-OS (German Published Specification) No. 2,201,432).

According to the state of the art, an acetoxyacetic acid anilide can be prepared, for example, by heating the corresponding chloroacetic acid anilide under reflux with a large excess of potassium acetate in dilute acetic acid for 20 hours.

After cooling the mixture, the acetoxyacetic acid anilide formed can then in general be isolated by filtration. The high consumption of potassium acetate as well as the contamination of the mother liquor by the excess acetate and by the potassium chloride formed as a concomitant product are to be regarded as the disadvantages of this process.

Saponification of the acetoxyacetic acid anilide is carried out, according to the state of the art, using 1 to 2 mol equivalents of an alkali metal hydroxide in methanol. In general, after neutralization, for example, with dilute hydrochloric acid, the glycollic acid anilide is separated out in the crystalline form. In this case also, the mother liquor contains relatively large amounts of salts. In addition, the yield and purity of the products thus obtained are not always completely satisfactory.

The present invention now provides a process for the preparation of an amide of the formula

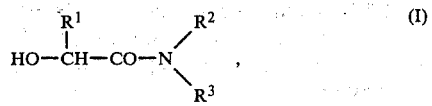  (I)

in which
R¹ represents hydrogen or alkyl and
R² and R³ are identical or different and each represent hydrogen or alkyl, alkenyl, alkynyl, aralkyl, cycloalkyl or aryl, in each case optionally substituted, or a nitrogen-containing heterocyclic radical, or
R² and R³, together with the nitrogen atom to which they are bonded, form an optionally substituted, optionally partially unsaturated and optionally benzo-fused monocyclic or bicyclic ring, which optionally contains one or more further heteroatoms, in which, in a first stage, an α-halogenocarboxylic acid amide of the general formula

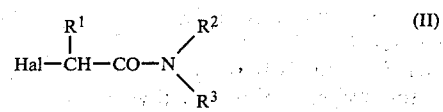  (II)

in which

R¹, R² and R³ have the meanings indicated above and Hal represents chlorine or bromine, is reacted with an alkali metal acetate or alkaline earth metal acetate in the presence of a quaternary ammonium salt and if appropriate using a diluent, at a temperature between 20° and 200° C., and, in a second stage, the α-acetoxycarboxylic acid amide prepared in this manner, of the general formula

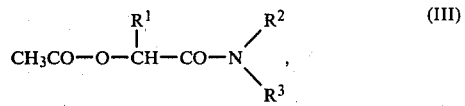  (III)

in which
R¹, R² and R³ have the meanings indicated above, is deacylated by reaction with an alcohol of the general formula

R⁴-OH  (IV), in which
R⁴ represents alkyl, in the presence of a catalytic amount of an alkali metal hydroxide or alkaline earth metal hydroxide or of an alkali metal carbonate or alkaline earth metal carbonate, at a temperature between 20° and 150° C.

It is to be described as surprising that in the reaction of α-halogenocarboxylic acid amides with equimolar amounts of an acetate, the corresponding α-acetoxycarboxylic acid amides can be formed in high purity and in almost quantitative yield, since, according to the state of the art, a larger excess of acetate is to be employed and only moderate yields are to be achieved. It is also surprising that the deacylation of the α-acetoxycarboxylic acid amides to give the α-hydroxycarboxylic acid amides using catalytic amounts of hydroxide can also give very pure products in a virtually quantitative yield.

In addition to the fact that it can be carried out simply, advantages of the process according to the invention are the use of the reagents in stoichiometric amount, the fact that there are no side-reactions, and the simple working up. Pollution of the environment with waste substances is thereby largely avoided, since the concomitant products and solvents can easily be separated off and isolated in a pure form.

If, for example, chloroacetic acid morpholide is used as the starting compound and sodium acetate in the first stage, and methanol, in the second stage, are used as reagents, the course of the reaction can be outlined by the following equation:

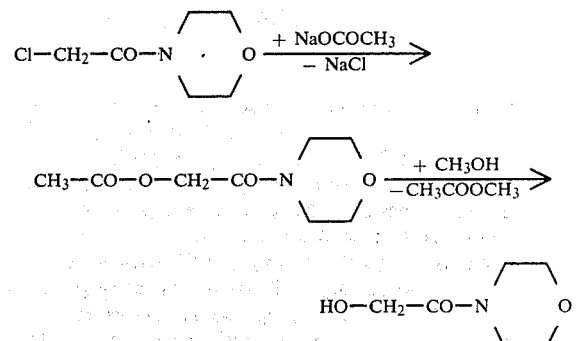

The formula (II) provides a definition of the α-halogenocarboxylic acid amides to be used as starting compounds. Preferably, in this formula R¹ represents hydrogen or methyl, R² and R³, which can be identical or different, each represents hydrogen, straight-chain or branched alkyl with 1 to 20 carbon atoms, cyanoalkyl with 2 to 5 carbon atoms, alkoxyalkyl with 2 to 8 carbon atoms, alkylthioalkyl with 2 to 8 carbon atoms, alkenyl with 3 to 10 carbon atoms, alkynyl with 3 to 10 carbon atoms, cycloalkyl with 3 to 12 carbon atoms, aralkyl with 1 to 2 carbon atoms in the alkyl part and 6 or 10 carbon atoms in the aryl part, aryl with 6 or 10 carbon atoms [it being possible for the two radicals last mentioned to carry one or more substituents selected from 1 to 3 halogen atoms (especially fluorine and/or chlorine and/or bromine), 1 to 3 alkyl radicals with in each case 1 to 4 carbon atoms, nitro and cyano], morpholinyl or tetrahydrofurfuryl, or R² and R³, together with the nitrogen atom to which they are bonded, form an optionally partially unsaturated and/or optionally benzo-fused monocyclic or bicyclic ring with 3 to 15 carbon atoms which is optionally substituted by 1 to 3 alkyl groups with in each case 1 to 5 carbon atoms (spiro-linked substituents with up to 4 carbon atoms and up to 2 oxygen atoms also being possible), and Hal preferably represents chlorine.

Particularly preferred starting substances are those compounds of formula (II)
wherein R¹ represents hydrogen, R² and R³, which can be identical or different, each represents straight-chain or branched alkyl with 1 to 10 carbon atoms, cyanoethyl, 2-alkoxyethyl with 1 to 5 (especially 1 to 3) carbon atoms in the alkoxy group, allyl, propargyl, 1-methylpropargyl, 1,1-dimethylpropargyl, cyclopentyl, cyclohexyl, phenyl, nitrophenyl, tolyl, nitrotolyl, chlorophenyl, naphthyl, benzyl, chlorobenzyl, chlorotolyl, morpholinyl or tetrahydrofurfuryl or, R² and R³, together with the nitrogen atom to which they are bonded, represent pyrrolidyl, monoalkyl- or dialkyl-pyrrolidyl with 1 to 5 (especially 1 to 3) C atoms per alkyl group, morpholinyl, monoalkyl- or dialkyl-morpholinyl with 1 to 5 (especially 1 to 3) C atoms per alkyl group, piperidyl, monoalkyl-, dialkyl- or trialkyl-piperidyl with in each case 1 to 5 (especially 1 to 3) C atoms per alkyl group, spiro-substituted piperidyl (especially the radical of the formula

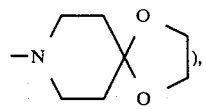

perhydro-azepinyl (=hexamethyleneimino radical), 1,2,3,4-tetrahydroindolyl, monoalkyl-, dialkyl- or trialkyl-1,2,3,4-tetrahydroindolyl with in each case 1 to 5 (especially 1 to 3) C atoms per alkyl group, perhydroindolyl, monoalkyl-, dialkyl- or trialkylperhydroindolyl with in each case 1 to 5 (especially 1 to 3) C atoms per alkyl group, 1,2,3,4-tetrahydroquinolyl, 1,2,3,4-tetrahydroisoquinolyl, monoalkyl-, dialkyl- or trialkyl-1,2,3,4-tetrahydroquinolyl or -isoquinolyl with in each case 1 to 5 (especially 1 to 3) C atoms per alkyl group, perhydroquinolyl or perhydroisoquinolyl, monoalkyl-, dialkyl- or trialkylperhydro-quinolyl or -isoquinolyl with in each case 1 to 5 (especially 1 to 3) C atoms per alkyl group, perhydrothiazolyl or the radical of the formula

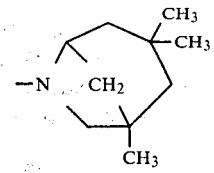

and

Hal represent chlorine.

Examples of the halogenocarboxylic acid amides of the formula (II) which may be mentioned are: chloroacetic acid methylamide, ethylamide, n-propylamide, iso-propylamide, n-butylamide, iso-butylamide, dimethylamide, diethylamide, di-n-propylamide, di-iso-propylamide, N-methyl-N-iso-propylamide, N-methyl-N-iso-butylamide, N-methyl-N-sec.-butylamide, di-(2-ethyl-hexyl)-amide, N-methyl-N-(2-cyano-ethyl)-amide, di-(2-methoxy-ethyl)-amide, diallylamide, N-methyl-N-propargylamide, N-methyl-N-(1-methyl-propargyl)-amide, dipropargylamide, cyclopentylamide, N-methyl-N-cyclopentylamide, cyclo-hexylamide, N-methyl-N-cyclohexylamide, anilide, 2-nitro-, 3-nitro- and 4-nitro-phenylamide, 2-chloro-, 3-chloro- and 4-chloro-phenylamide, 2,4-dichloro-, 2,5-dichloro, 3,4-dichloro- and 3,5-dichloro-phenylamide, 2-methyl-, 3-methyl- and 4-methyl-phenylamide, N-methylanilide, N-methyl-N-(2-methyl-phenyl)-amide, N-methyl-N-(2-nitrophenyl)-, N-methyl-N-(3-nitrophenyl)- and N-methyl-N-(4-nitrophenyl)-amide, N-methyl-N-(2-chlorophenyl)-, N-methyl-N-(3-chlorophenyl)- and N-methyl-N-(4-chlorophenyl)-amide, N-methyl-N-(3-nitro-6-methyl-phenyl)-amide, N-ethylanilide, N-ethyl-N-(2-nitro-phenyl)-, N-ethyl-N-(3-nitro-phenyl)- and N-ethyl-N-(4-nitro-phenyl)-amide, N-ethyl-N-(2-chloro-phenyl)-, N-ethyl-N-(3-chloro-phenyl)- and N-ethyl-N-(4-chloro-phenyl)-amide, N-ethyl-N-(3-nitro-6-methylphenyl)-amide, N-propyl-anilide, N-propyl-N-(2-nitro-phenyl)-, N-propyl-N-(3-nitro-phenyl)- and N-propyl-N-(4-nitro-phenyl)-amide, N-propyl-N-(2-chloro-phenyl)-, N-propyl-N-(3-chloro-phenyl)- and N-propyl-N-(4-chloro-phenyl)-amide, N-propyl-N-(2-methyl-phenyl)-, N-propyl-N-(3-methyl-phenyl)- and N-propyl-N-(4-methyl-phenyl)-amide, N-propyl-N-(3-nitro-6-methyl-phenyl)-amide, N-butyl-anilide, N-butyl-N-(2-nitro-phenyl)-, N-butyl-N-(3-nitro-phenyl)- and N-butyl-N-(4-nitro-phenyl)-amide, N-butyl-N-(2-chloro-phenyl)-, N-butyl-N-(3-chloro phenyl)- and N-butyl-N-(4-chloro-phenyl)-amide, N-butyl-N-(2-methyl-phenyl)-, N-butyl-N-(3-methyl-phenyl)- and N-butyl-N-(4-methyl-phenyl)-amide, N-butyl-N-(3-nitro-6-methyl-phenyl)-amide, N-isobutyl-anilide, N-iso-butyl-N-(2-nitro-phenyl)-, N-iso-butyl-N-(3-nitro-phenyl) and N-iso-butyl-N-(4-nitro-phenyl)-amide, N-iso-butyl-N-(2-chloro-phenyl)-, N-iso-butyl-N-(3-chloro-phenyl)- and N-iso-butyl-N-(4-chloro-phenyl)-amide, N-iso-butyl-N-(2-methyl-phenyl)-, N-iso-butyl-N-(3-methyl-phenyl)- and N-iso-butyl-N-(4-methyl-phenyl)-amide, N-iso-butyl-N-(3-nitro-6-methyl-phenyl)-amide, naphth-1-ylamide, naphth-2-ylamide, N-methyl-N-naphth-1-ylamide, N-methyl-N-naphth-2-ylamide, N- ethyl-N-naphth-1-ylamide, N-ethyl-N-naphth-2-ylamide, N-n-propyl-N-naphth-2-ylamide, N-iso-propyl-N-naphth-2-ylamide, N-n-butyl-N-naphth-2-ylamide, N-iso-butyl-N-naphth-2-ylamide, benzylamide, dibenzylamide, N-methyl-N-benzylamide, N-ethyl-N-benzylamide, N-propyl-N-benzylamide, N-butyl-N-benzylamide, pyrrolidide, 2-methyl-pyrrolidide, morpholide, piperidide, 2-methyl-piperidide, 4-methyl-piperidide, 2,4-dimethyl-piperidide, 2,4,6-trimethyl-piperidide, 2-ethyl-piperidide, 4-ethyl-piperidide, 2,4-diethyl-piperidide, 2,4,6-triethyl-piperidide, 2-methyl-4-ethyl-piperidide, 2-ethyl-4-methyl-piperidide, 2-methyl-5-ethyl-piperidide, 2-ethyl-5-methyl-piperidide, 2-methyl-6-ethyl-piperidide, 1,2,3,4-tetrahydroindolide, 2-methyl-1,2,3,4-tetrahydroindolide, perhydroindolide, 2-methyl-perhydroindolide, 2,2-dimethyl-perhydroindolide, 1,2,3,4-tetrahydroindolide, 2-methyl-1,2,3,4-tetrahydroquinolide, perhydroquinolide, 2-methyl-perhydroquinolide, 4-methyl perhydroquinolide, 1,2,3,4-tetrahydroiso-quinolide and perhydroisoquinolide.

The α-halogenocarboxylic acid amides of the formula (II) are known, or they can be prepared analogously to known processes, for example by reacting α-halogenocarboxylic acid halides, for example chloroacetyl chloride, with ammonia or primary or secondary amines, if appropriate in the presence of an acid acceptor, for example, potassium hydroxide (see J. Agric. Food Chem. 4 (1956), 518–522).

The alkali metal acetates or alkaline earth metal acetates to be used as reagents in the first process stage are known. Examples which may be mentioned are sodium acetate and potassium acetate.

Quaternary ammonium salts are used as catalysts in the first process stage. Possible quaternary ammonium salts are tetraalkylammonium salts, it being possible for the alkyl radicals independently of one another to contain 1 to 4 carbon atoms. Trialkyl-aralkylammonium salts with 1 to 4 carbon atoms per alkyl radical and with 1 to 2 carbon atoms in the alkyl part of the aralkyl radical and 6 or 10 carbon atoms in the aryl part of the aralkyl radical can also be used as catalysts.

Examples which may be mentioned are tetra-n-butylammonium bromide and benzyltrimethylammonium chloride.

Alkali metal hydroxides or alkaline earth metal hydroxides or alkali metal carbonates or alkaline earth metal carbonates are used as catalysts in the second process stage.

Examples of these which may be mentioned are sodium hydroxide, potassium hydroxide, calcium hydroxide, sodium carbonate and potassium carbonate.

Formula (IV) provides a definition of the alcohols to be used as reagents and simultaneously as diluents in the second process stage. In this formula, $R^4$ preferably represents straight-chain or branched alkyl with 1 to 4 carbon atoms.

Examples which may be mentioned are methanol, ethanol and n- and iso-propanol.

The first process stage is preferably carried out using suitable solvents or diluents. Suitable solvents or diluents are virtually any of the inert organic solvents. These include, as preferences, aliphatic and aromatic, optionally chlorinated hydrocarbons, such as benzine, benzene, toluene, xylene, methylene chloride, chloroform, carbon tetrachloride, ethylene chloride, chlorobenzene and o-dichlorobenzene; ethers, such as diethyl ether, dibutyl ether, tetrahydrofuran and dioxan; ketones, such as acetone, methyl ethyl ketone, methyl isopropyl ketone and methyl isobutyl ketone; and nitriles, such as acetonitrile and propionitrile.

The reaction temperatures are, for the first stage, in general between 20° and 200° C., preferably between 50° and 150° C., and for the second stage, between 20° and 150° C., preferably between 50° and 120° C. Both stages of the process according to the invention are in general carried out under normal pressure.

In carrying out the process according to the invention, in the first stage 0.9 to 1.5 moles, preferably 0.95 to 1.2 moles, of acetate (anhydrous) are generally employed per mole of α-halogenocarboxylic acid amide (II) and 1 to 20 mmoles, preferably 2 to 15 mmoles, of ammonium salt catalyst are used. The reactants are in general heated to the required reaction temperature in one of the diluents indicated for some hours and the mixture is cooled and, after filtration, the diluent is distilled off. To carry out the second process stage, the α-acetoxycarboxylic acid amide which remains in the residue in this procedure is heated in 2 to 5 mol equivalents of one of the alcohols indicated above in the presence of 1 to 100 mmoles, preferably 5 to 50 mmoles, of hydroxide or carbonate for some hours. After distilling off the excess of alcohol and the ester formed as a concomitant product, the α-hydroxycarboxylic acid amide is obtained in the residue and is optionally purified by recrystallisation. The α-hydroxycarboxylic acid amides are in general obtained in high purity by the process according to the invention and can be used without additional purification processes.

The α-hydroxy-carboxylic acid amides which can be prepared according to the invention can be used as intermediate products for the preparation of herbicides (see for example, U.S. Pat. No. 3,399,988, DE-OS (German Offenlegungsschrift) No. 2,201,432 and DE-OS (German Offenlegungsschrift) No. 2,647,568).

PREPARATIVE EXAMPLES

Example 1

(a) Intermediate product:

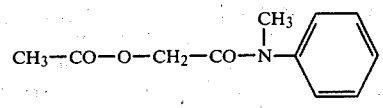

A suspension of 183.5 g (1 mol) of chloroacetic acid N-methylanilide, 82 g (1 mol) of anhydrous sodium acetate, 0.5 g of benzyltrimethylammonium chloride and 320 ml of toluene was heated to 115°–120° C. for 4 hours and then cooled to room temperature. The mixture was filtered and the residue was rinsed with cold toluene. After distilling off the solvent from the toluene solution and evaporating the residue under a steam jet vacuum at a bath temperature of 80°–85° C., 207 g of α-acetoxy-acetic acid N-methylanilide, which crystallized on standing, were obtained. GC(analysis by gas chromatography):=98% pure; melting point=54°–56° C.; yield=99% of theory.

(b) End product

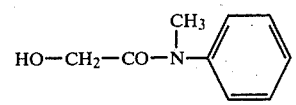

A reaction mixture of 211.2 g (1 mol) of α-acetoxyacetic acid N-methylanilide (98% pure), 0.2 g of sodium hydroxide and 160 g of methanol was heated under reflux for 4 hours. A mixture of methanol and methyl acetate was distilled off. The liquid distillation residue [a quantitative yield of 170 g of hydroxy-acetic acid N-methylanilide; GC=98% pure; melting point=52°-53° C.] solidified on cooling.

Example 2

(a) Intermediate product

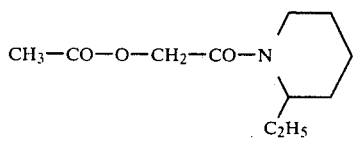

A suspension of 32.8 g (0.169 mol) of chloroacetic acid 2-ethylpiperidine (97.8% pure), 14.4 g (0.175 mol) of sodium acetate (anhydrous), 0.5 g of benzyltrimethylammonium chloride and 50 ml of toluene was heated to 115°-120° C. for 5 hours. After cooling the reaction mixture to room temperature, the inorganic residue was filtered off and washed with toluene. After distilling off the solvent from the toluene solution and evaporating the residue at a bath temperature of 80°-85° C. under a steam jet vacuum, 36.1 g of liquid α-acetoxyacetic acid 2-ethyl-piperidide were obtained in a yield of 96.7% of theory; GC: 96.4% pure.

(b) End product

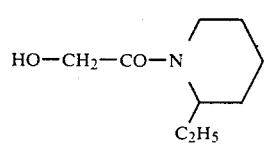

A reaction mixture of 22 g (0.1 mol) of α-acetoxyacetic acid 2-ethylpiperidide (97% pure), 0.2 g of potassium hydroxide and 50 ml of methanol was heated under reflux for 5 hours. A mixture of methanol and methyl acetate was distilled off. A liquid distillation residue consisting of hydroxy-acetic acid 2-ethyl-piperidide in a yield of 97.3% of theory was obtained; GC: 97.3% pure.

The compounds of the formula (I) or (III) listed in the tables below, for example could be prepared by procedures analogous to those of Example 1 or 2:

TABLE I

Compounds of the formula $$CH_3-CO-O-\underset{\underset{R^1}{|}}{CH}-CO-N\underset{R^3}{\overset{R^2}{\diagup}} \quad (III)$$

| Example No. | $R^1$ | $-N\underset{R^3}{\overset{R^2}{\diagup}}$ | Yield (% of theory) | Melting point (°C.) Refractive index |
|---|---|---|---|---|
| 3(a) | H |  | 99 | |
| 4(a) | H |  | | |
| 5(a) | H | $-N(CH_2-CH_2-OCH_3)_2$ | 91 | $n_D^{25}$ 1.4880 |
| 6(a) | H |  | 100 | $n_D^{25}$ 1.4816 |
| 7(a) | H |  | 98 | $n_D^{25}$ 1.4718 |
| 8(a) | H | 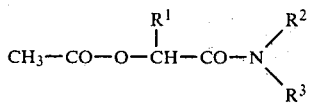 | | |
| 9(a) | H |  | | |
| 10(a) | H |  | 91 | $n_D^{25}$ 1.4760 |
| 11(a) | H |  | 80 | $n_D^{24}$ 1.4997 |
| 12(a) | H |  | | |
| 13(a) | H |  | | |
| 14(a) | H |  | 69 | 97° |
| 15(a) | H |  | 87 | $n_D^{25}$ 1.4932 |
| 16(a) | H | $-N(CH_2-CH=CH_2)_2$ | 100 | $n_D^{25}$ 1.4748 |

TABLE II

Compounds of the formula $$HO-\overset{R^1}{\underset{}{C}H}-CO-N\overset{R^2}{\underset{R^3}{}}  \quad (I)$$

| Example No. | $R^1$ | $-N\overset{R^2}{\underset{R^3}{}}$ | Yield (% of theory) | Melting point (°C.) Refractive index |
|---|---|---|---|---|
| 3(b) | H | 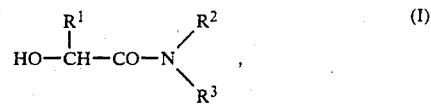 | 100 | 36° |
| 4(b) | H | -N(morpholino) | | |
| 5(b) | H | $-N(CH_2-CH_2-OCH_3)_2$ | 100 | $n_D^{25}$ 1,4662 |
| 6(b) | H | -N(CH₃)(cyclohexyl) | 100 | 83° |
| 7(b) | H | $-N(CH_3)-CH(CH_3)-C\equiv CH$ | 97,4 | $n_D^{25}$ 1,4859 |
| 8(b) | H | $-N(CH_3)-CH(CH_3)-C_2H_5$ | | |
| 9(b) | H | 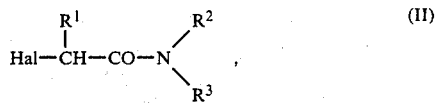 | | |
| 10(b) | H | -N(naphthyl)(iso-C₃H₇) | | |
| 11(b) | H | -N(2,6-dimethylpiperidino) | 60 | $n_D^{23}$ 1,4816 |
| 12(b) | H | -N(decahydroquinolinyl) | 65 | 55° C. |
| 13(b) | H | -N(tetrahydroquinolinyl) | 70 | $n_D^{23}$ 1,5076 |
| 14(b) | H | -N(tetrahydroisoquinolinyl) | 61 | 80° |
| 15(b) | H | 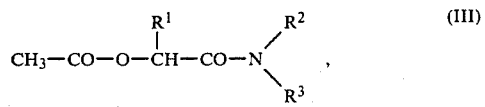 | 63 | |
| 16(b) | H | $-N(CH_2-CH=CH_2)_2$  | | |

It will be understood that the specification and examples are illustrative, but not limitative of the present invention and that other embodiments within the spirit and scope of the invention will suggest themselves to those skilled in the art.

What is claimed is:

1. Process for the preparation of an alpha-hydrocarboxylic acid amide compound of the formula $$HO-\overset{R^1}{\underset{}{C}H}-CO-N\overset{R^2}{\underset{R^3}{}}  \quad (I)$$

wherein
$R^1$ is hydrogen or alkyl; and
$R^2$ and $R^3$ are individually selected from hydrogen, alkyl, alkenyl, alkynyl, aralkyl, cycloalkyl or aryl, each of which may be optionally substituted, or a nitrogen-containing heterocyclic radical; or
$R^2$ and $R^3$, together with the nitrogen atom to which they are bonded, represent an optionally benzo-fused monocyclic or bicyclic ring, which ring may be substituted and may be partially unsaturated, which process comprises reacting in a first stage an alpha-halocarboxylic acid amide of the formula $$Hal-\overset{R^1}{\underset{}{C}H}-CO-N\overset{R^2}{\underset{R^3}{}}  \quad (II)$$

wherein
$R^1$, $R^2$ and $R^3$ are identified as above with the proviso that $R^1$, $R^2$ and $R^3$ are not all hydrogen; and
Hal is chlorine or bromine, with an alkali metal acetate or alkaline earth metal acetate in the presence of a quaternary ammonium salt and as a diluent wherein the reactants are suspended, an aliphatic or aromatic optionally chlorinated hydrocarbon, at a temperature between 20° and 200° C., and, in a second stage, deacylating the alpha-acetoxycarboxylic acid amide produced, having the general formula $$CH_3-CO-O-\overset{R^1}{\underset{}{C}H}-CO-N\overset{R^2}{\underset{R^3}{}}  \quad (III)$$

in which $R^1$, $R^2$ and $R^3$, are identified as above by reacting said amide III with an alcohol of the general formula $$R^4\text{-OH} \quad (IV),$$

in which $R^4$ is alkyl in the presence of a catalytic amount of a catalyst selected from alkali metal hydroxides, alkaline earth metal hydroxides, alkali metal carbonates, and alkaline earth metal carbonates, at a temperature between 20° and 150° C.

2. Process as claimed in claim 1 in which the said first stage of the reaction is carried out at a temperature between 50° C. and 150° C.

3. Process as claimed in claim 1 in which the said second stage of the reaction is carried out at a temperature between 50° C. and 120° C.

4. Process as claimed in claim 1 wherein a tetraalkylammonium salt with 1 to 4 carbon atoms per alkyl radical or a trialkyl-aralkylammonium salt with 1 to 4 carbon atoms per alkyl radical and with 1 or 2 carbon atoms in the alkyl part of the aralkyl radical and 6 or 10 carbon atoms in the aryl part of the aralkyl radical is employed as the quaternary ammonium salt.

5. Process as claimed in claim 1 wherein a tetra-n-butylammonium bromide or benzyltrimethylammonium chloride is employed as the quaternary ammonium salt.

6. Process as claimed in claim 1 wherein, in the first stage, 0.9 to 1.5 moles of acetate (anhydrous) and 1 to 20 mmoles of the quaternary ammonium salt are employed per mole of amide (II).

7. Process as claimed in claim 6 wherein 0.95 to 1.2 moles of acetate (anhydrous) and 2 to 15 mmoles of quaternary ammonium salt are employed per mole of amide (II).

8. Process as claimed in claim 1 wherein, in the second stage, 2 to 5 mol equivalents of alcohol (IV) and 1 to 100 mmoles of an alkali metal hydroxide or alkaline earth metal hydroxide or of an alkali metal carbonate or alkaline earth metal carbonate are employed with the alpha-acetoxycarboxylic acid amide (III) obtained per mole of the alpha-halocarboxylic acid amide (II).

9. Process as claimed in claim 8 wherein 5 to 50 mmoles of an alkali metal hydroxide or alkaline earth metal hydroxide or of an alkali metal carbonate or alkaline earth metal carbonate are employed with the alpha-acetoxycarboxylic acid amide (III) obtained per mole of the alpha-halocarboxylic acid (II).

10. Process as claimed in claim 1 wherein a compound of formula (II) is used wherein
$R^1$ is hydrogen or methyl,
$R^2$ and $R^3$ are individually selected from hydrogen, alkyl with 1 to 20 carbon atoms, cyanoalkyl with 2 to 5 carbon atoms, alkoxyalkyl with 2 to 8 carbon atoms, alkylthioalkyl with 2 to 8 carbon atoms, alkenyl with 3 to 10 carbon atoms, alkynyl with 3 to 10 carbon atoms, cycloalkyl with 3 to 12 carbon atoms, aralkyl with 1 to 2 carbon atoms in the alkyl part and 6 or 10 carbon atoms in the aryl part, aryl with 6 or 10 carbon atoms, it being possible for the last two mentioned radicals to carry one or more substituents selected from 1 to 3 halogen atoms, 1 to 3 alkyl radicals with, in each case, 1 to 4 carbon atoms, nitro and cyano; morpholinyl or tetrahydrofurfuryl, or
$R^2$ and $R^3$, together with the nitrogen atom to which they are bonded, represent an optionally benzofused monocyclic or bicyclic ring with 3 to 15 carbon atoms which is optionally substituted by 1 to 3 alkyl groups with, in each case, 1 to 5 carbon atoms (spiro-linked substituents with up to 4 carbon atoms and up to 2 oxygen atoms also being possible), and
Hal is chlorine.

11. Process as claimed in claim 1 wherein a compound of formula (II) is used wherein
$R^1$ represents hydrogen,
$R^2$ and $R^3$, which can be identical or different, each represent straight-chain or branched alkyl with 1 to 10 carbon atoms, cyanoethyl, 2-alkoxyethyl with 1 to 5 carbon atoms in the alkoxy group, allyl, propargyl, 1-methylpropargyl, 1,1-dimethylpropargyl, cyclopentyl, cyclohexyl, phenyl, nitrophenyl, tolyl, nitrotolyl, chlorophenyl, naphthyl, benzyl, chlorobenzyl, chlorotolyl, morpholinyl or tetrahydrofurfuryl, or
$R^2$ and $R^3$ together with the nitrogen atom to which they are bonded, represent pyrrolidyl, monoalkyl- or dialkyl-pyrrolidyl with 1 to 5 carbon atoms per alkyl group, morpholinyl, monoalkyl- or dialkyl-morpholinyl with 1 to 5 carbon atoms per alkyl group, piperidyl, monoalkyl-, dialkyl- or trialkyl-piperidyl with in each case 1 to 5 carbon atoms per alkyl group, spiro-substituted piperidyl, perhydroazepinyl, 1,2,3,4-tetrahydroindolyl, monoalkyl-, dialkyl- or trialkyl-1,2,3,4-tetrahydroindolyl with in each case 1 to 5 carbon atoms per alkyl group, perhydroindolyl, monoalkyl-, dialkyl- or trialkyl-perhydroindolyl with in each case 1 to 5 carbon atoms per alkyl group, 1,2,3,4-tetrahydro-quinolyl, 1,2,3,4-tetrahydro-iso-quinolyl, monoalkyl-, dialkyl- or trialkyl-1,2,3,4-tetrahydro-quinolyl or -isoquinolyl with in each case 1 to 5 carbon atoms per alkyl group, perhydroquinolyl or perhydroisoquinolyl, monoalkyl-, dialkyl- or trialkyl-perhydro-quinolyl or -isoquinolyl with in each case 1 to 5 carbon atoms per alkyl group, perhydrothiazolyl or the radical of the formula

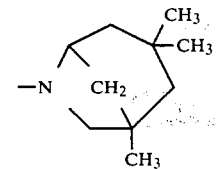

and
Hal represents chlorine.

12. Process as claimed in claim 1 wherein hydroxyacetic acid N-methylanilide is produced from alpha-acetoxyacetic acid N-methylanilide.

13. Process as claimed in claim 1 wherein hydroxyacetic acid 2-methylpiperidide is produced from alpha-acetoxyacetic acid 2-methylpiperidide.

14. Process as claimed in claim 1 wherein hydroxyacetic acid N-methyl-N-cyclohexylamine is produced from alpha-acetoxyacetic acid N-methyl-N-cyclohexylamide.

15. Process as claimed in claim 1 wherein hydroxyacetic acid N-methyl-N-(1-methylpropargyl)-amide is produced from alpha-acetoxyacetic acid N-methyl-N-(1-methylpropargyl)-amide.

16. Process as claimed in claim 1 wherein hydroxyacetic acid N,N-di-(2-propenyl)amide is produced from alpha-acetoxyacetic acid N,N-di-(2-propenyl)amide.

* * * * *